(12) United States Patent　　　　(10) Patent No.:　US 12,678,152 B2
Doctor et al.　　　　　　　　　　　　(45) Date of Patent:　Jul. 14, 2026

(54) TISSUE-CUTTING DILATORS AND METHODS THEREOF

(71) Applicant: Bard Access Systems, Inc., Salt Lake City, UT (US)

(72) Inventors: Liam Doctor, Salt Lake City, UT (US); Joshua D. Sherwood, Cottonwood Heights, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 634 days.

(21) Appl. No.: 17/982,119

(22) Filed: Nov. 7, 2022

(65) Prior Publication Data

US 2023/0141739 A1　　May 11, 2023

Related U.S. Application Data

(60) Provisional application No. 63/277,002, filed on Nov. 8, 2021.

(51) Int. Cl.
A61B 17/02　　　(2006.01)
A61M 29/02　　　(2006.01)
(52) U.S. Cl.
CPC ......... A61B 17/0206 (2013.01); A61M 29/02 (2013.01); A61M 2029/025 (2013.01)
(58) Field of Classification Search
CPC ............ A61B 17/0206; A61B 17/3417; A61B 17/3496; A61B 2017/3454;
(Continued)

(56) References Cited

U.S. PATENT DOCUMENTS 2,566,499 A　　9/1951　Richter
2,842,133 A　　7/1958　Uhma
(Continued)

FOREIGN PATENT DOCUMENTS

CN　　　2456639 Y　　10/2001
CN　　210844555 U　　6/2020
(Continued)

OTHER PUBLICATIONS

PCT/US2023/012270 filed Feb. 3, 2023 International Search Report and Written Opinion dated Jun. 21, 2023.
(Continued)

*Primary Examiner* — Tan-Uyen T Ho
*Assistant Examiner* — Bridget E. Rabaglia
(74) *Attorney, Agent, or Firm* — Rutan & Tucker LLP

(57)　　　　　　ABSTRACT

A tissue-cutting dilator can include an elongate dilator body, a dilator tip, a plurality of retractable blades, and a cap. The dilator body can include a plurality of longitudinal guide slots along a distal portion of the dilator body. The dilator tip can be formed in the distal portion of the dilator body or coupled to a distal end of the dilator body. The dilator tip can include a plurality of blade slots. The blades can be disposed in the dilator body. The blades can be configured to extend through the blade slots in a ready-to-dilate state of the dilator to cut tissue around an insertion site upon insertion into the insertion site. The cap can be slidably disposed over the dilator body. The cap can cover the dilator tip in at least the ready-to-dilate state of the dilator.

20 Claims, 13 Drawing Sheets

(58) Field of Classification Search
CPC .......... A61B 17/32093; A61B 17/3209; A61B 17/3213; A61B 90/02; A61B 2017/32096; A61M 29/02; A61M 2029/025; A61M 29/00; A61M 25/0074; A61M 25/104

See application file for complete search history.

(56) References Cited

U.S. PATENT DOCUMENTS

| | | |
|---|---|---|
| 3,921,631 A | 11/1975 | Thompson |
| 4,324,044 A | 4/1982 | Shahinian, Jr. |
| 4,392,856 A | 7/1983 | Lichtenstein |
| 4,601,710 A | 7/1986 | Moll |
| 4,693,250 A | 9/1987 | Coons |
| 4,889,112 A | 12/1989 | Schachner et al. |
| 4,955,890 A | 9/1990 | Yamamoto et al. |
| 5,279,285 A | 1/1994 | Griggs |
| 5,334,157 A | 8/1994 | Klein et al. |
| 5,509,900 A | 4/1996 | Kirkman |
| 5,578,009 A | 11/1996 | Kraus et al. |
| 5,728,073 A | 3/1998 | Whisson |
| 5,755,697 A | 5/1998 | Jones et al. |
| 5,800,450 A | 9/1998 | Lary et al. |
| 5,843,115 A | 12/1998 | Morejon |
| 6,033,388 A | 3/2000 | Nordstrom et al. |
| 6,517,519 B1 | 2/2003 | Rosen et al. |
| 6,544,277 B1 * | 4/2003 | O'Heeron .......... A61B 17/3417 |
| | | 606/167 |
| 6,761,725 B1 | 7/2004 | Grayzel et al. |
| 9,114,227 B2 | 8/2015 | Blanchard |
| 9,480,498 B1 | 11/2016 | Kessler |
| 10,028,762 B1 | 7/2018 | Slupchynskyj |
| 10,188,403 B2 | 1/2019 | Mirochinik et al. |
| 10,376,675 B2 | 8/2019 | Mitchell et al. |
| 10,603,071 B1 | 3/2020 | Whitman et al. |
| 2002/0040231 A1 | 4/2002 | Wysoki |
| 2002/0161387 A1 * | 10/2002 | Blanco ............... A61B 17/3494 |
| | | 606/167 |
| 2002/0165600 A1 | 11/2002 | Banas et al. |
| 2002/0177864 A1 | 11/2002 | Camrud |
| 2003/0074013 A1 | 4/2003 | Schooler et al. |
| 2004/0133227 A1 | 7/2004 | Shang et al. |
| 2004/0181246 A1 | 9/2004 | Heppler |
| 2004/0181273 A1 | 9/2004 | Brasington et al. |
| 2005/0177183 A1 | 8/2005 | Thorne et al. |
| 2009/0024089 A1 | 1/2009 | Levine et al. |
| 2009/0076435 A1 | 3/2009 | Melsheimer et al. |
| 2009/0125030 A1 | 5/2009 | Tebbe et al. |
| 2010/0057056 A1 | 3/2010 | Gurtner et al. |
| 2012/0130417 A1 | 5/2012 | Lepulu et al. |
| 2012/0226299 A1 | 9/2012 | Heppler |
| 2013/0197558 A1 | 8/2013 | Ingold, Jr. et al. |
| 2016/0128713 A1 | 5/2016 | Rauchwerger et al. |
| 2016/0220786 A1 | 8/2016 | Mitchell et al. |
| 2016/0346503 A1 | 12/2016 | Jackson et al. |
| 2017/0128700 A1 | 5/2017 | Roche Rebollo |
| 2017/0296792 A1 | 10/2017 | Ornelas Vargas et al. |
| 2019/0307485 A1 | 10/2019 | Kiev |
| 2019/0351183 A1 | 11/2019 | Ishida |
| 2020/0061322 A1 | 2/2020 | De Rezende Neto |
| 2020/0086095 A1 | 3/2020 | Kleinhaus |
| 2020/0155190 A1 | 5/2020 | Basadonna et al. |
| 2020/0222077 A1 | 7/2020 | Takahashi |
| 2020/0246597 A1 | 8/2020 | Broniec et al. |
| 2021/0069471 A1 | 3/2021 | Howell |
| 2021/0085927 A1 | 3/2021 | Howell |
| 2021/0106351 A1 | 4/2021 | Hossack et al. |
| 2021/0113809 A1 | 4/2021 | Howell |
| 2021/0113810 A1 | 4/2021 | Howell |
| 2021/0121661 A1 | 4/2021 | Howell |
| 2021/0212722 A1 * | 7/2021 | Kiev .................. A61B 17/3415 |
| 2022/0087708 A1 | 3/2022 | Chen et al. |
| 2022/0152368 A1 | 5/2022 | Thornley et al. |
| 2022/0176081 A1 | 6/2022 | Spataro et al. |
| 2023/0233227 A1 | 7/2023 | Lindekugel et al. |
| 2023/0241353 A1 | 8/2023 | Howell et al. |
| 2023/0241354 A1 | 8/2023 | Howell |
| 2023/0255660 A1 | 8/2023 | Howell |
| 2023/0255661 A1 | 8/2023 | Howell |
| 2023/0277212 A1 | 9/2023 | Howell |
| 2023/0277813 A1 | 9/2023 | Howell |
| 2023/0277814 A1 | 9/2023 | Howell |

FOREIGN PATENT DOCUMENTS

| | | |
|---|---|---|
| CN | 111481303 A | 8/2020 |
| CN | 112155683 A | 1/2021 |
| DE | 10100332 A1 | 7/2002 |
| DE | 202004012605 U1 | 10/2004 |
| EP | 0507607 A1 | 10/1992 |
| EP | 3852564 A1 | 7/2021 |
| GB | 2245148 A | 1/1992 |
| WO | 9108709 A1 | 6/1991 |
| WO | 9412091 A1 | 6/1994 |
| WO | 02087666 A2 | 11/2002 |
| WO | 03022129 A2 | 3/2003 |
| WO | 2011024013 A1 | 3/2011 |
| WO | 2011057282 A2 | 5/2011 |
| WO | 2012087506 A2 | 6/2012 |
| WO | 2016176065 A1 | 11/2016 |
| WO | 2017006323 A1 | 1/2017 |
| WO | 2020057677 A1 | 3/2020 |
| WO | 2020076691 A1 | 4/2020 |
| WO | 2022104149 A1 | 5/2022 |
| WO | 2022120201 A1 | 6/2022 |
| WO | 2023081465 A1 | 5/2023 |
| WO | 2023122313 A1 | 6/2023 |
| WO | 2023141170 A1 | 7/2023 |
| WO | 2023150263 A1 | 8/2023 |
| WO | 2023150314 A1 | 8/2023 |
| WO | 2023158643 A1 | 8/2023 |
| WO | 2023158645 A1 | 8/2023 |
| WO | 2023167943 A1 | 9/2023 |
| WO | 2023168005 A1 | 9/2023 |
| WO | 2023168097 A1 | 9/2023 |

OTHER PUBLICATIONS

PCT/US2023/012345 filed Feb. 3, 2023 International Search Report and Written Opinion dated Jun. 27, 2023.

PCT/US2023/013056 filed Feb. 14, 2023 International Search Report and Written Opinion dated Jun. 12, 2023.

PCT/US2023/013058 filed Jun. 7, 2023 International Search Report and Written Opinion dated Jun. 7, 2023.

PCT/US2023/014298 filed Mar. 1, 2023 International Search Report and Written Opinion dated Jun. 1, 2023.

PCT/US2023/014375 filed Mar. 2, 2023 International Search Report and Written Opinion dated Jun. 7, 2023.

PCT/US2023/014384 filed Mar. 2, 2023 International Search Report and Written Opinion dated Jun. 16, 2023.

PCT/US2023/014532 filed Mar. 3, 2023 International Search Report and Written Opinion dated Jul. 10, 2023.

U.S. Appl. No. 17/542,096, filed Dec. 3, 2021 Non Final Office Action dated Jun. 1, 2023.

U.S. Appl. No. 17/525,774, filed Nov. 12, 2021 Advisory Action dated Aug. 26, 2024.

U.S. Appl. No. 17/525,774, filed Nov. 12, 2021 Final Office Action dated Jun. 18, 2024.

U.S. Appl. No. 17/542,096, filed Dec. 3, 2021 Final Office Action dated Aug. 1, 2024.

PCT/US2021/059256 filed Nov. 12, 2021 International Search Report and Written Opinion dated Mar. 23, 2022.

PCT/US2021/061857 filed Dec. 3, 2021 International Search Report and Written Opinion dated Apr. 11, 2022.

Rauchwerger, Jacob Jeffrey, Michael Serle, and Jeffrey C. Astbury. "Novel Wire-Guided Scalpel to Facilitate Central Venous Catheter Insertion without a Skin Bridge." Vascular Specialist International 37 (2021).

PCT/US2022/049134 filed Nov. 7, 2022 International Search Report and Written Opinion dated Mar. 30, 2023.

(56) References Cited

OTHER PUBLICATIONS

PCT/US2022/053889 filed Dec. 22, 2022 International Search Report and Written Opinion dated Apr. 20, 2023.

PCT/US2023/011067 filed Jan. 18, 2023 International Search Report and Written Opinion dated May 11, 2023.

U.S. Appl. No. 17/542,096, filed Dec. 3, 2021 Restriction Requirement dated Mar. 1, 2023.

U.S. Appl. No. 17/525,774, filed Nov. 12, 2021 Non-Final Office Action dated Jan. 24, 2024.

U.S. Appl. No. 17/542,096, filed Dec. 3, 2021 Advisory Action dated Nov. 29, 2023.

U.S. Appl. No. 17/542,096, filed Dec. 3, 2021 Final Office Action dated Sep. 20, 2023.

U.S. Appl. No. 17/542,096, filed Dec. 3, 2021 Non-Final Office Action dated Jan. 18, 2024.

U.S. Appl. No. 17/525,774, filed Nov. 12, 2021 Non-Final Office Action dated Jan. 28, 2025.

U.S. Appl. No. 17/542,096, filed Dec. 3, 2021 Non-Final Office Action dated Dec. 27, 2024.

U.S. Appl. No. 17/542,096, filed Dec. 3, 2021 Notice of Allowance dated May 9, 2025.

U.S. Appl. No. 18/098,607, filed Jan. 18, 2023 Non-Final Office Action dated Feb. 6, 2025.

U.S. Appl. No. 18/116,748, filed Mar. 2, 2023 Non-Final Office Action dated May 21, 2025.

U.S. Appl. No. 17/525,774, filed Nov. 12, 2021 Notice of Allowance dated Jul. 18, 2025.

U.S. Appl. No. 18/087,699, filed Dec. 22, 2022 Non-Final Office Action dated Sep. 10, 2025.

U.S. Appl. No. 18/098,607, filed Jan. 18, 2023 Final Office Action dated Aug. 11, 2025.

U.S. Appl. No. 18/105,357, filed Feb. 3, 2023 Non-Final Office Action dated Oct. 2, 2025.

U.S. Appl. No. 18/105,743, filed Feb. 3, 2023 Non-Final Office Action dated Oct. 2, 2025.

U.S. Appl. No. 18/109,793, filed Feb. 14, 2023 Non-Final Office Action dated Oct. 1, 2025.

U.S. Appl. No. 18/109,793, filed Feb. 14, 2023 Restriction Requirement dated Jul. 17, 2025.

U.S. Appl. No. 18/117,334, filed Mar. 3, 2023 Restriction Requirement dated Oct. 30, 2025.

U.S. Appl. No. 18/109,793, filed Feb. 14, 2023 Notice of Allowance dated Mar. 5, 2026.

U.S. Appl. No. 18/117,334, filed Mar. 3, 2023 Non-Final Office Action dated Mar. 26, 2026.

* cited by examiner

TISSUE-CUTTING DILATORS AND METHODS THEREOF

PRIORITY

This application claims the benefit of priority to U.S. Provisional Patent Application No. 63/277,002, filed Nov. 8, 2021, which is incorporated by reference in its entirety into this application.

BACKGROUND

Before placing a catheter in a blood vessel of a patient, it is common to nick the patient's skin about a needle tract at an insertion site for dilation of tissue therearound with a dilator. Typically, nicking the patient's skin and dilating the tissue around the needle tract is performed separately. Indeed, the nicking is usually performed with a dedicated skin nicker or a scalpel having a #11 blade; the dilating is usually performed with a dilator two French sizes larger than the catheter being placed. Attempts to integrate the nicking of the patient's skin and the dilating of the tissue around the needle tract have resulted in a spring-loaded blade generally regarded as unsafe due to clinicians not being able to control the blade. What is needed is a tissue-cutting dilator that safely integrates the nicking of a patient's skin at an insertion site with the dilating of tissue around a needle tract at the insertion site. Such a dilator would reduce procedural time and errors when, for example, placing a catheter at the insertion site.

Disclosed herein are tissue-cutting dilators and methods thereof that address the foregoing.

SUMMARY

Disclosed herein a tissue-cutting dilator including, in some embodiments, an elongate dilator body, a dilator tip, a plurality of retractable blades, and a cap. The dilator body includes a plurality of longitudinal guide slots along a distal portion of the dilator body. The dilator tip is formed in the distal portion of the dilator body or coupled to a distal end of the dilator body. The dilator tip includes a plurality of blade slots. The blades are disposed in the dilator body. The blades are configured to extend through the blade slots in at least a ready-to-dilate state of the dilator to cut tissue around an insertion site upon insertion into the insertion site. The cap is slidably disposed over the dilator body. The cap covers the dilator tip in at least the ready-to-dilate state of the dilator.

In some embodiments, the guide slots terminate as grooves in the dilator tip. The grooves provide reinforcing structure to the dilator tip over that provided by the guide slots for tissue dilation with the dilator tip.

In some embodiments, distal ends of the blades are short of a distal end of the dilator or the dilator tip thereof. Having distal ends of the blades short of the distal end of the dilator or the dilator tip thereof allows at least the distal end of the dilator tip to engage the insertion site before cutting the tissue around the insertion site.

In some embodiments, the blades include two intersecting blades coupled to a catch plate slidably disposed in the dilator body proximal of the dilator tip.

In some embodiments, the two intersecting blades provide four orthogonal blade edges. Each blade edge of the foregoing blade edges is orthogonal to its immediately adjacent blade edges.

In some embodiments, the catch plate is proximal of the distal tip in the ready-to-dilate state of the dilator.

In some embodiments, the cap includes a plurality of cap protrusions protruding toward a central axis of the dilator. The cap protrusions are disposed in at least a distal portion of the cap such that the cap protrusions slide in the guide slots and engage the catch plate when proximally sliding the cap over the dilator body past the dilator tip. Engaging the catch plate when proximally sliding the cap over the dilator body past the dilator tip retracts the blades into the dilator body for subsequent dilation with the dilator without further cutting the tissue around the insertion site.

In some embodiments, the cap is configured to proximally slide over the dilator body by interaction with skin around the insertion site as the dilator tip is inserted into the insertion site.

In some embodiments, the catch plate includes a plurality of notches configured to engage the cap protrusions in the distal portion of the cap. The notches in the catch plate are orthogonal to the blades.

In some embodiments, the cap protrusions are further disposed in a proximal portion of the cap. The cap protrusions in the proximal portion of the cap are configured to slide in the guide slots and obviate any play between the proximal portion of the cap and the dilator body thereunder.

In some embodiments, the catch plate includes a stabilizer integral with the catch plate or coupled to a proximal end of the catch plate. The stabilizer includes split legs configured to slidably engage an inner wall of the dilator body and mitigate tilting of the catch plate within the dilator body. Mitigating tilting of the catch plate within the dilator body keeps the blades properly aligned in the dilator body, thereby avoiding blade jams.

In some embodiments, the dilator further includes a compression spring. The compression spring is between a proximal end of the catch plate and a seat therefor in the dilator body. The compression spring is configured to mitigate tilting of the catch plate within the dilator body. Mitigating tilting of the catch plate within the dilator body keeps the blades properly aligned in the dilator body, thereby avoiding blade jams.

In some embodiments, the compression spring is further configured to keep the blades extending through the blade slots in the ready-to-dilate state of the dilator whether or not the dilator is pointed, in part, along a gravitational vector.

Also disclosed herein is another tissue-cutting dilator including, in some embodiments, an elongate dilator body, a dilator tip, and a pair of rotatable blades. The dilator tip is formed in the distal portion of the dilator body or coupled to a distal end of the dilator body. Each blade of the blades has an approximate shape of a geometric disk sector ⊙ with a blade edge along an arc thereof. Each blade of the blades is disposed in an opposite side of the dilator such that the blades cut tissue on opposite sides of an insertion site upon insertion of the dilator into the insertion site.

In some embodiments, the blades are short of a distal end of the dilator or the dilator tip thereof. Having the blades short of the distal end of the dilator or the dilator tip thereof allows at least the distal end of the dilator tip to engage the insertion site before cutting the tissue around the insertion site.

In some embodiments, each blade of the blades includes a primary tissue catch extending from a leading corner of the blade where a leading edge meets the blade edge. The primary tissue catch is configured to catch the tissue around the insertion site, rotate the blade out from the dilator body, and cut the tissue around the insertion site as the dilator is inserted into the insertion site.

In some embodiments, just the primary tissue catch extends from its respective side of the dilator in a ready-to-dilate state of the dilator.

In some embodiments, each blade of the blades includes a secondary tissue catch in a midsection of the blade edge. The secondary tissue catch is configured to further catch the tissue around the insertion site, further rotate the blade out from the dilator body, and further cut the tissue around the insertion site as the dilator is further inserted into the insertion site.

In some embodiments, each blade of the blades includes a tertiary tissue catch extending from a trailing corner of the blade where a trailing edge meets the blade edge. The tertiary tissue catch is configured to catch the tissue around the insertion site and rotate the blade into the dilator body without further cutting the tissue around the insertion site as the dilator is inserted into the insertion site.

In some embodiments, each blade of the blades is rotatably mounted on a pin of a pair of pins disposed in a pinhole of a pair of pinholes of a supporting frame. The frame is optionally divided between sides of the dilator including the blades.

In some embodiments, each pin of the pair or pins is disposed in a junction between the dilator body and the dilator tip.

In some embodiments, the frame is disposed in a middle of the dilator along a longitudinal plane of symmetry.

Also disclosed herein is a method of a tissue-cutting dilator including, in some embodiments, a dilator-inserting step, a tissue-cutting step, and a ceasing step. The dilator-inserting step includes inserting a dilator tip of the dilator into an insertion site. The dilator-inserting step commences dilation of tissue around the insertion site. The tissue-cutting step includes cutting the tissue around the insertion site with a plurality of blades while further inserting the dilator tip into the insertion site. The blades are disposed in the dilator short of a distal end of the dilator or the dilator tip thereof. The ceasing step includes ceasing to cut the tissue around the insertion site with the blades while even further inserting the dilator tip into the insertion site. The blades either retract or rotate into the dilator while even further inserting the dilator tip into the insertion site.

In some embodiments, a cap of the dilator is made to proximally slide over the dilator by interaction with skin around the insertion site while inserting the dilator tip into the insertion site during the dilator-inserting step. Proximally sliding the cap over the dilator exposes the blades for the cutting of the tissue around the insertion site.

In some embodiments, the blades include two intersecting blades coupled to a catch plate slidably disposed in a dilator body of the dilator. The catch plate is disposed in the dilator body proximal of the dilator tip.

In some embodiments, the two intersecting blades provide four orthogonal blade edges. Each blade edge of the foregoing blade edges is orthogonal to its immediately adjacent blade edges.

In some embodiments, the cap is further made to proximally slide over the dilator by the interaction with the skin around the insertion site while further inserting the dilator tip into the insertion site during the tissue-cutting step. Proximally sliding the cap further over the dilator keeps the blades exposed for the cutting of the tissue around the insertion site.

In some embodiments, the cap is even further made to proximally slide over the dilator by the interaction of the skin around the insertion site while even further inserting the dilator tip into the insertion site during the ceasing step. Proximally sliding the cap even further over the dilator makes cap protrusions of the cap extending through guide slots of the dilator to engage the catch plate and retract the blades into the dilator for the ceasing to cut the tissue around the insertion site with the blades.

In some embodiments, primary tissue catches of the blades in corresponding leading corners of the blades extend from sides of the dilator and catch skin around the insertion site while inserting the dilator tip into the insertion site during the dilator-inserting step. Catching skin around the insertion site while inserting the dilator tip into the insertion site rotates the blades out of the dilator for the cutting of the tissue around the insertion site.

In some embodiments, secondary tissue catches of the blades in midsections of the blades catch the tissue around the insertion site while further inserting the dilator tip into the insertion site during the tissue-cutting step. Catching skin around the insertion site while further inserting the dilator tip into the insertion site continues to rotate the blades out of the dilator for the cutting of the tissue around the insertion site.

In some embodiments, tertiary tissue catches of the blades in corresponding trailing corners of the blades catch the tissue around the insertion site while even further inserting the dilator tip into the insertion site during the ceasing step. Catching skin around the insertion site while even further inserting the dilator tip into the insertion site rotates the blades into the dilator for the ceasing to cut the tissue around the insertion site with the blades.

These and other features of the concepts provided herein will become more apparent to those of skill in the art in view of the accompanying drawings and following description, which describe particular embodiments of such concepts in greater detail.

DRAWINGS

DESCRIPTION

Figures 1, 2, 3:
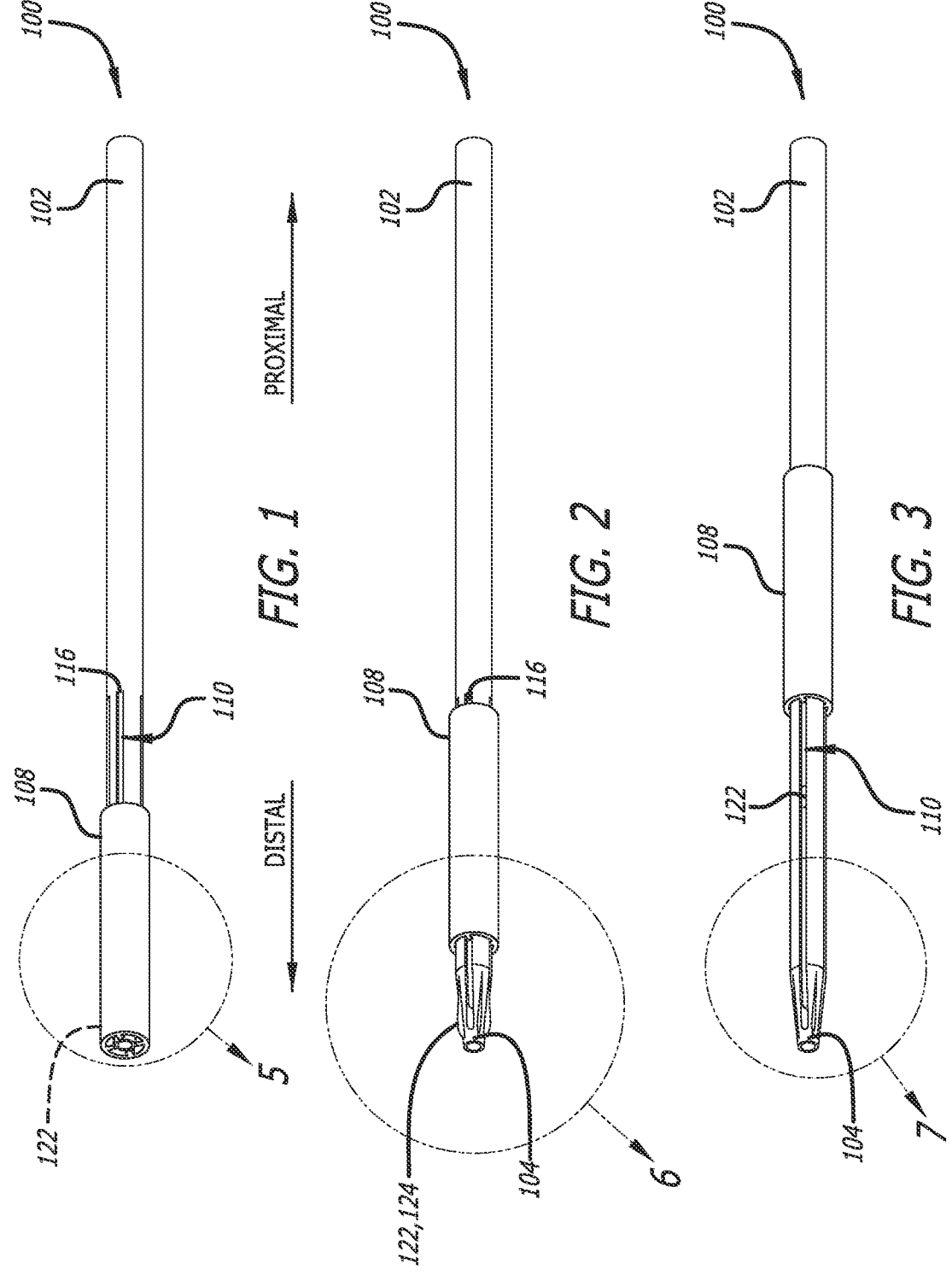
FIG. 1 illustrates a first tissue-cutting dilator in a ready-to-dilate state with a cap over a dilator tip, the cap thereby covering retractable blades that extend through blade slots of the dilator tip in accordance with some embodiments.
FIG. 2 illustrates the first dilator in a relatively early dilating state with the cap over a proximal portion of a dilator body, the cap thereby exposing the blades that extend through the blade slots of the dilator tip in accordance with some embodiments.
FIG. 3 illustrates the first dilator in a relatively late dilating state with the cap over a medial portion of the dilator body, the blades retracted into the dilator body in accordance with some embodiments.
Figures 4, 5:
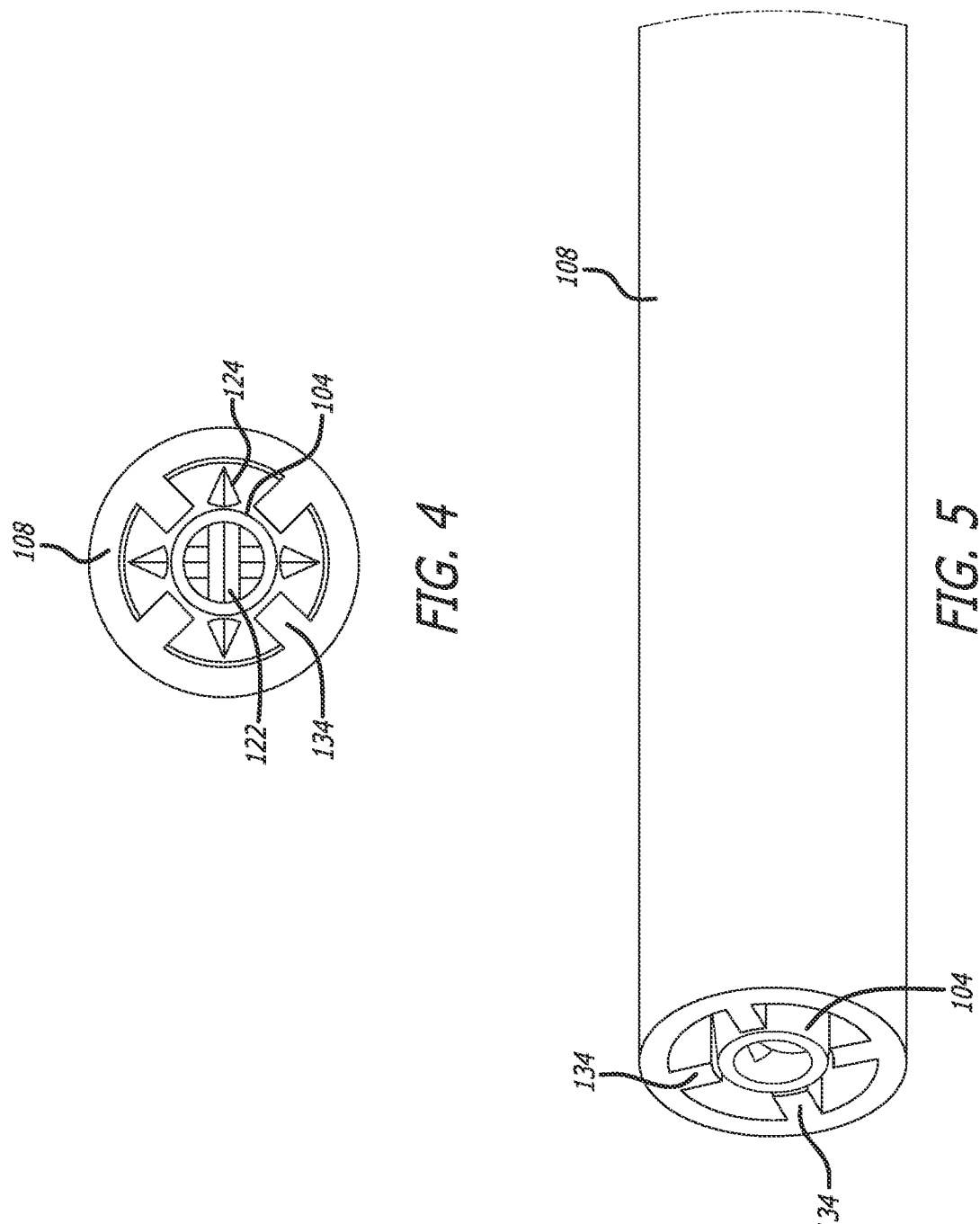
FIG. 4 illustrates an end-on view of a distal end of the first dilator in the ready-to-dilate state thereof in accordance with some embodiments.
FIG. 5 illustrates a detailed view of a distal portion of the first dilator in the ready-to-dilate state thereof in accordance with some embodiments.
Figures 6, 7:
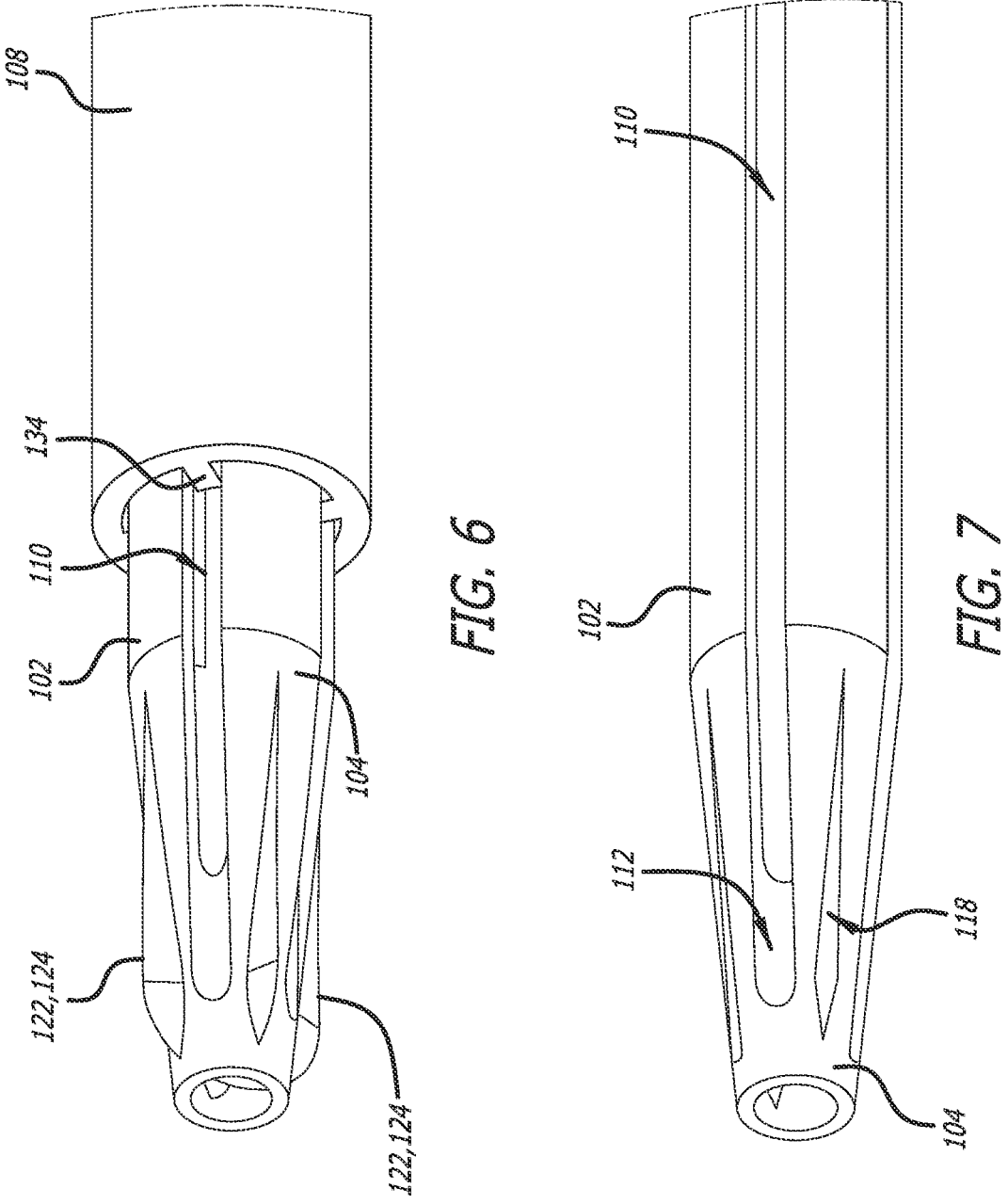
FIG. 6 illustrates a detailed view of the distal portion of the first dilator in the relatively early dilating state thereof in accordance with some embodiments.
FIG. 7 illustrates a detailed view of the distal portion of the first dilator in the relatively late dilating state thereof in accordance with some embodiments.
Figures 8, 9, 10:
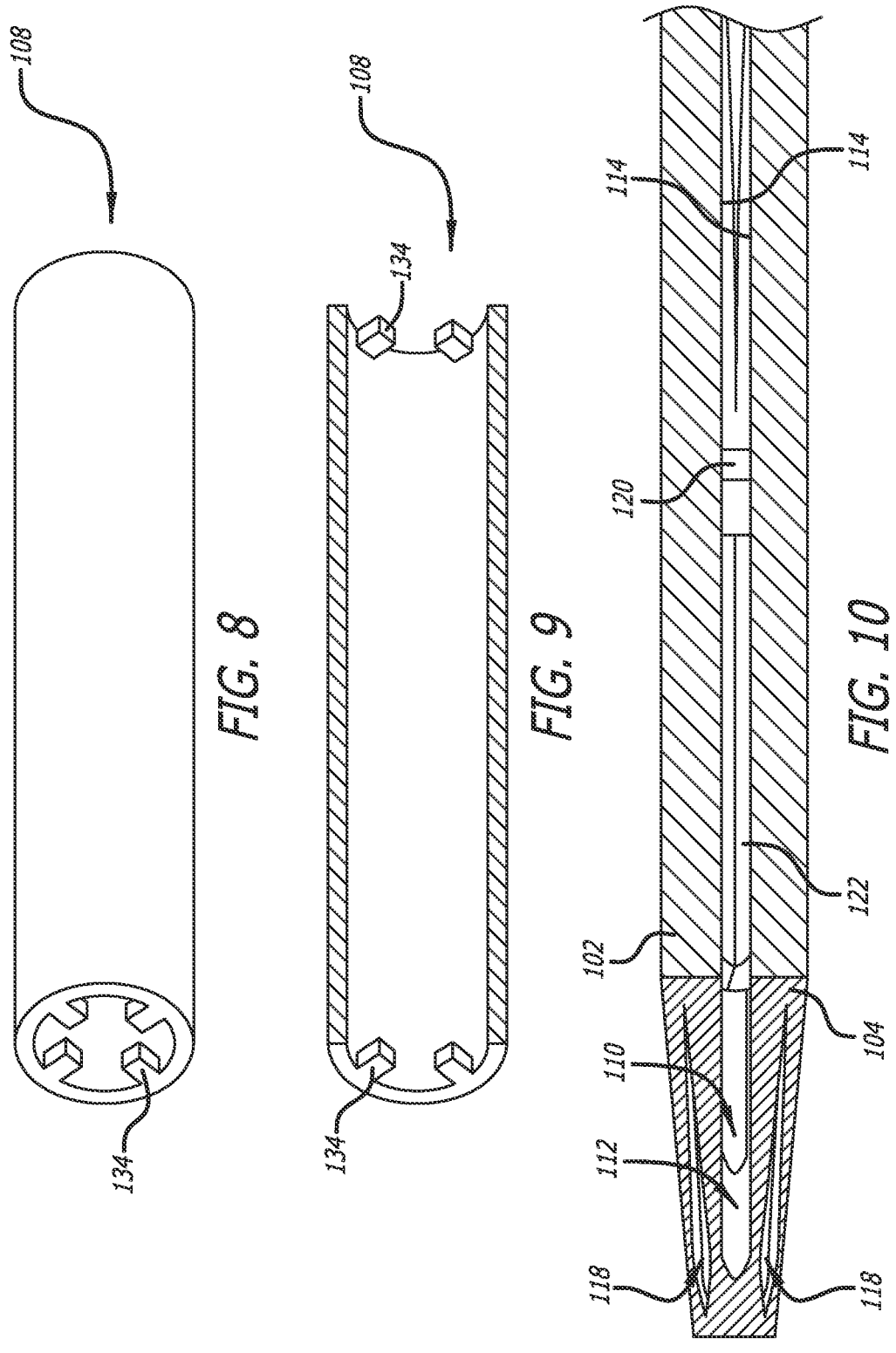
FIG. 8 illustrates a detailed view of the cap of the first dilator in accordance with some embodiments.
FIG. 9 illustrates a longitudinal cross section of the cap of the first dilator in accordance with some embodiments.
FIG. 10 illustrates a detailed view of at least the distal portion of the first dilator without the cap in the relatively late dilating state thereof in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or "proximal section" of, for example, a tissue-cutting dilator includes a portion or section of the dilator intended to be near a clinician when the dilator is used on a patient. Likewise, a "proximal length" of, for example, the dilator includes a length of the dilator intended to be near the clinician when the dilator is used on the patient. A "proximal end" of, for example, the dilator includes an end of the dilator intended to be near the clinician when the dilator is used on the patient. The proximal portion, the proximal section, or the proximal length of the dilator can include the proximal end of the dilator; however, the proximal portion, the proximal section, or the proximal length of the dilator need not include the proximal end of the dilator. That is, unless context suggests otherwise, the proximal portion, the proximal section, or the proximal length of the dilator is not a terminal portion or terminal length of the dilator.

With respect to "distal," a "distal portion" or a "distal section" of, for example, a tissue-cutting dilator includes a portion or section of the dilator intended to be near or in a patient when the dilator is used on the patient. Likewise, a "distal length" of, for example, the dilator includes a length of the dilator intended to be near or in the patient when the dilator is used on the patient. A "distal end" of, for example, the dilator includes an end of the dilator intended to be near or in the patient when the dilator is used on the patient. The distal portion, the distal section, or the distal length of the dilator can include the distal end of the dilator; however, the distal portion, the distal section, or the distal length of the dilator need not include the distal end of the dilator. That is, unless context suggests otherwise, the distal portion, the distal section, or the distal length of the dilator is not a terminal portion or terminal length of the dilator.

Unless defined otherwise, all technical and scientific terms used herein have the same meaning as commonly understood by those of ordinary skill in the art.

As set forth above, it is common to nick a patient's skin about a needle tract at an insertion site for dilation of tissue therearound with a dilator before placing a catheter in a blood vessel of the patient. Typically, nicking the patient's skin and dilating the tissue around the needle tract is performed separately. Indeed, the nicking is usually performed with a dedicated skin nicker or a scalpel having a #11 blade; the dilating is usually performed with a dilator two French sizes larger than the catheter being placed. Attempts to integrate the nicking of the patient's skin and the dilating of the tissue around the needle tract have resulted in a spring-loaded blade generally regarded as unsafe due to clinicians not being able to control the blade. What is needed is a tissue-cutting dilator that safely integrates the nicking of a patient's skin at an insertion site with the dilating of tissue around a needle tract at the insertion site. Such a dilator would reduce procedural time and errors when, for example, placing a catheter at the insertion site.

Disclosed herein are tissue-cutting dilators and methods thereof that address the foregoing.

Dilators

FIGS. 1-17 illustrate a first tissue-cutting dilator 100 in accordance with some embodiments.

As shown, the dilator 100 includes an elongate dilator body 102, a dilator tip 104, a blade carriage 106, and a cap 108.

The dilator body 102 includes a plurality of longitudinal guide slots 110 along a distal portion of the dilator body 102. The guide slots 110 distally terminate with open-ended grooves 112 in the dilator tip 104, which grooves 112 provide reinforcing structure (e.g., connecting or bridging portions) to the dilator tip 104 over that provided by the guide slots 110 for tissue dilation with the dilator tip 104. The guide slots 110 and the grooves 112 are configured to accept therein the cap protrusions 134 for proximally sliding the cap 108 over the dilator body 102. Notably, one or more of the guide slots 110 can include up to at least a pair of guide-slot catches 114 per guide slot. Such catches are configured to restrict the cap 108 from distally sliding over the dilator tip 104 in the ready-to-dilate state of the dilator 100 by inhibiting the cap protrusions 134 in the proximal portion of the cap 108, which cap protrusions are proximal of the guide-slot catches 114 in the ready-to-dilate state of the dilator 100, from passing thereby. Such catches are also configured to restrict the cap 108 from distally sliding back over the dilator body 102 in later dilating states of the dilator 100 by inhibiting the cap protrusions 134 in the distal portion of the cap 108, which are proximal of the guide-slot catches 114 in the later dilating states of the dilator 100, from passing thereby. In addition, the guide slots 110 proximally terminate with terminal ends 116 in, for example, a medial portion of the dilator body 102. Such terminal ends are configured to restrict the cap 108 from proximally sliding too far over the dilator body 102 by inhibiting the cap protrusions 134 in either the proximal or distal portion of the cap 108 from passing thereby.

The dilator tip 104 is formed in the distal portion of the dilator body 102 or coupled to a distal end of the dilator body 102. The dilator tip 104 includes a plurality of blade slots 118 orthogonal to the guide slots 110 configured for extending the blades 122 therethrough. Notably, distal ends of the blade slots 118 are short of a distal end of the dilator 100 or the dilator tip 104 thereof. Having distal ends of the blade slots 118 short of the distal end of the dilator 100 or the dilator tip 104 thereof allows at least the distal end of the dilator tip 104 to engage an insertion site before cutting tissue around the insertion site with the blades 122.

The blade carriage 106 is slidably disposed in the dilator body 102 such that a catch plate 120 thereof is proximal of the dilator tip 104 in the ready-to-dilate state of the dilator 100. The blade carriage 106 includes a plurality of retractable blades 122 coupled to the catch plate 120, the blades 122 being retractable in accordance with proximally sliding the blade carriage 106 with the cap 108 when the cap 108 is proximally slid over the dilator body 102.

The blades 122 are configured to extend through the blade slots 118 in at least a ready-to-dilate state of the dilator 100 for cutting tissue around an insertion site upon insertion into the insertion site. However, distal ends of the blades 122 are short of the distal end of the dilator 100 or the dilator tip 104 thereof. Having distal ends of the blades 122 short of the distal end of the dilator 100 or the dilator tip 104 thereof allows at least the distal end of the dilator tip 104 to engage an insertion site before cutting tissue around the insertion site with the blades 122.

The blades 122 can include two intersecting blades coupled to the catch plate 120; however, the blades 122 are not limited to the two intersecting blades as fewer or more of the blades 122 can be used with or without intersecting to a same or different effect. That said, the two intersecting blades provide four orthogonal blade edges 124, wherein each blade edge of the blade edges 124 is orthogonal to its immediately adjacent blade edges 124. Advantageously, the blades 122 cut tissue in an 'X'-style cut along two orthogonal planes with comparatively shorter individual cuts along the two orthogonal planes than that required in existing methods such as those set forth above. Such an 'X'-style cut of the tissue maximizes the so-called opening response of the tissue, leading to less tension in the tissue and, thus, a lower insertion force, thereby reducing damage to the tissue.

The catch plate 120 can include one or more slots or recesses 126 in which proximal ends of the blades 122 are disposed with transition- or interference-type engineering fits. In addition to the foregoing engineering fits, or as an alternative to them, the proximal ends of the blades 122 can be bonded to the one-or-more slots or recesses 126 of the catch plate 120.

Figures 11, 12, 13:
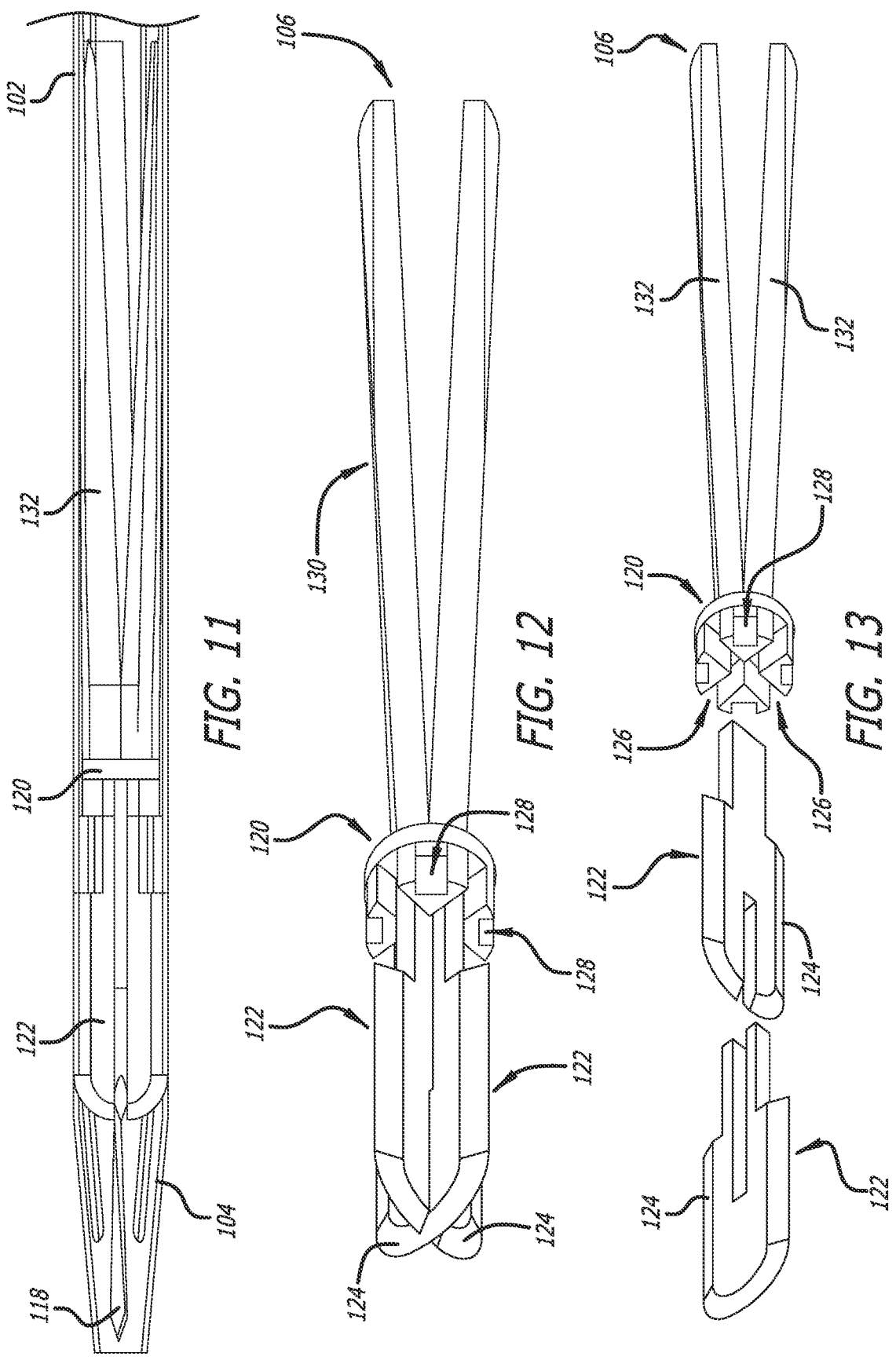
FIG. 11 illustrates a longitudinal cross section of at least the distal portion of the first dilator without the cap in the relatively late dilating state thereof, the dilator including a first blade carriage in accordance with some embodiments.
FIG. 12 illustrates the first blade carriage of the first dilator in accordance with some embodiments.
FIG. 13 illustrates an exploded view of the first blade carriage in accordance with some embodiments.
Figures 14, 15, 16:
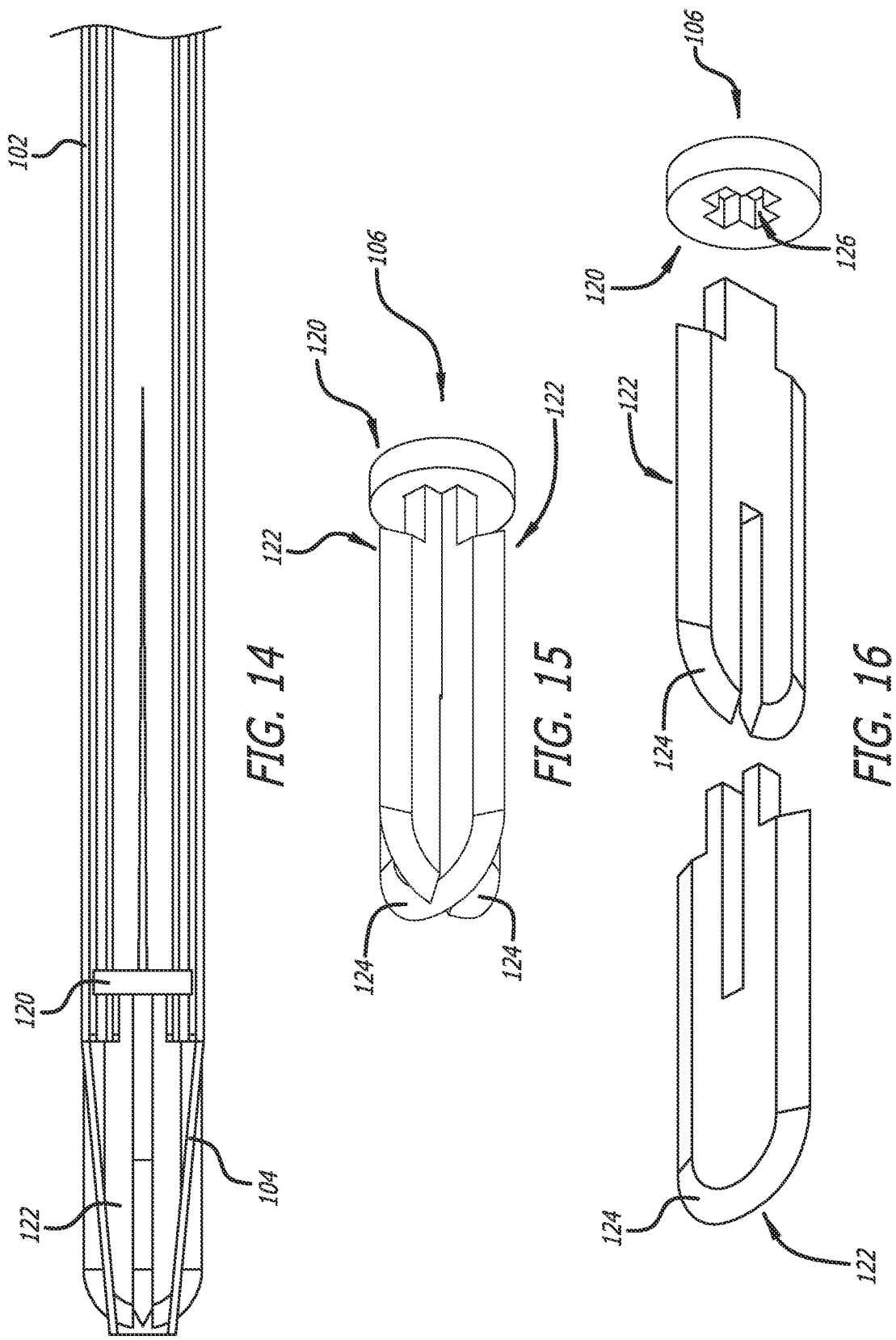
FIG. 14 illustrates a longitudinal cross section of at least the distal portion of the first dilator without the cap in the relatively late dilating state thereof, the dilator including a second blade carriage in accordance with some embodiments.
FIG. 15 illustrates the second blade carriage of the first dilator in accordance with some embodiments.
FIG. 16 illustrates an exploded view of the second blade carriage in accordance with some embodiments.

The catch plate 120 can include a plurality of distally opening notches 128 configured to engage the cap protrusions 134 in the distal portion of the cap 108. Indeed, the notches 128 engaging the cap protrusions 134 when proximally sliding the cap 108 over the dilator body 102 past the dilator tip 104 proximally slides the blade carriage 106 in the dilator body 102, thereby retracting the blades 122 into the dilator body 102 for subsequent dilation of an insertion site with the dilator 100 without further cutting tissue around the insertion site. While the notches 128 can vary in number in accordance with the cap protrusions 134, FIG. 12 illustrates four orthogonal notches, wherein each notch of the notches 128 is orthogonal to its immediately adjacent notches 128; however, the notches 128 in the catch plate 120 are isogonally staggered with the blade edges 124, the proximal ends of the blades 122, or the one-or-more slots or recess 126 in the catch plate 120 by 45° to provide maximal circumferential clearance between the blade edges 124 and the cap protrusions 134.

The catch plate 120 can include a stabilizer 130 integral with the catch plate 120 or coupled to a proximal end of the catch plate 120. The stabilizer 130 includes split legs 132 configured to slidably engage an inner wall of the dilator body 102. Notwithstanding the terminal ends 116 of the guide slots 110, the split legs 132 of the stabilizer 130 in combination with, for example, one or more inner-wall protrusions protruding from the inner wall of the dilator body 102, are configured to form a stopping mechanism in a proximal portion of the dilator body 102 for stopping the blade carriage 106 from proximally sliding too far in the dilator body 102. Advantageously, when the stabilizer 130, the one-or-more inner-wall protrusions, and the guide-slot catches 114 are present in the dilator 100, the blade carriage 106 can be locked into a proximal location in the dilator body 102 by a combination of the cap protrusions 134 proximal of the guide-slot catches 114 in the guide slots 110, the cap protrusions 134 disposed in the notches 128 of the catch plate 120, and the split legs 132 of the stabilizer 130 distal of the one the one-or-more inner-wall protrusions when the blade carriage 106 is proximally slid to that location while dilating with the dilator 100. In this way, the foregoing features provide an integrated single-use enforcement mechanism enforcing a single use of each dilator like the dilator 100. Notably, the stabilizer 130 can mitigate tilting of the catch plate 120 within the dilator body 102. Mitigating the tilting of the catch plate 120 within the dilator body 102 keeps the blades 122 properly aligned in the dilator body 102, thereby avoiding blade jams against, for example, the inner wall of the dilator body 102 or that of the dilator tip 104 adjacent the blade slots 118 when the blade carriage 106 is proximally slid in the dilator body 102.

The cap 108 is slidably disposed over the dilator body 102. The cap 108 covers the dilator tip 104 providing a safeguard with respect to the blades 122 extending through the blade slots 118 of the dilator tip 104 in at least the ready-to-dilate state of the dilator 100. Notably, the cap 108 is configured to proximally slide over the dilator body 102 by interaction with skin around an insertion site as the dilator tip 104 is inserted into a needle tract at the insertion site. Indeed, as the dilator tip 104 is advanced into the needle tract, the skin around the insertion site pushes the cap 108 such that it proximally slides over the dilator body 102.

The cap 108 includes a plurality of cap protrusions 134 protruding toward a central axis of the dilator 100. The cap protrusions 134 are disposed in at least a distal portion of the cap 108 such that the cap protrusions 134 slide in the guide slots 110 and engage the notches 128 of the catch plate 120 when proximally sliding the cap 108 over the dilator body 102 past the dilator tip 104. The cap protrusions 134 engaging the notches 128 of the catch plate 120 when proximally sliding the cap 108 over the dilator body 102 past the dilator tip 104 proximally slides the blade carriage 106 in the dilator body 102, thereby retracting the blades 122 into the dilator body 102 for subsequent dilation of an insertion site with the dilator 100 without further cutting tissue around the insertion site. Notably, the cap protrusions 134 or a protruding annulus can be further disposed in a proximal portion of the cap 108. The cap protrusions 134 in the proximal portion of the cap 108 can be configured to slide in the guide slots 110 and obviate any play between the proximal portion of the cap 108 and the dilator body 102 thereunder. That said, the cap protrusions 134 or the protruding annulus in the proximal portion of the cap 108 can be configured to slide over the dilator body 102 outside of the guide slots 110 and likewise obviate any play between the proximal portion of the cap 108 and the dilator body 102 thereunder.

While not shown, the dilator 100 can further include a compression spring. When present, the compression spring can be between and, optionally, coupled to the proximal end of the catch plate 120 and a seat for the compression spring in the dilator body 102 like that of the one-or-more inner walls set forth above. When present, the compression spring keeps the blades 122 of the blade carriage 106 extending through the blade slots 118 of the dilator tip 104 in the ready-to-dilate state of the dilator 100 whether or not the dilator 100 is pointed, in part, along a gravitational vector. Like the stabilizer 130, the compression spring can also mitigate the tilting of the catch plate 120 within the dilator body 102. As set forth above, mitigating the tilting of the catch plate 120 within the dilator body 102 keeps the blades 122 properly aligned in the dilator body 102, thereby avoiding blade jams.

FIGS. 8-29 illustrate a second tissue-cutting dilator 200 in accordance with some embodiments.

As shown, the dilator 200 includes an elongate dilator body 202, a dilator tip 204, a supporting frame 236, and a pair of rotatable blades 238.

The dilator tip 204 is formed in the distal portion of the dilator body 202 or coupled to a distal end of the dilator body 202. Regardless, the dilator 200 includes a pair of blade slots 240 in sides of the dilator 200 between the dilator tip 204 and the dilator body 202 configured for rotating the blades 238 out of the dilator 200 in a ready-to-dilate state of the dilator 200 and back into the dilator 200 in a mid-dilating state to a relatively late-dilating state of the dilator 200. Notably, distal ends of the blade slots 240 are short of a distal end of the dilator 200 or the dilator tip 204 thereof. Having distal ends of the blade slots 240 short of the distal end of the dilator 200 or the dilator tip 204 thereof allows at least the distal end of the dilator tip 204 to engage an insertion site before cutting tissue around the insertion site with the blades 238.

The frame 236 is disposed in a middle of the dilator 200 between the dilator tip 204 and the dilator body 202 in support of the blades 238 and their rotation out of the dilator 200 in the ready-to-dilate state of the dilator 200 and back into the dilator 200 in the mid-dilating state to the relatively late-dilating state of the dilator 200. The frame 236 is optionally a single piece, two pieces divided between top and bottom halves of the dilator 200 defined as being on opposite sides of a first longitudinal plane of symmetry of the dilator 200 including the frame 236 and the blades 238, or four pieces divided between the top and bottom halves of the dilator 200 as well as sinistral and dextral sides of the dilator 200 defined as being on opposite sides of a second longitudinal plane of symmetry of the dilator 200 orthogonal to the first longitudinal plane of symmetry. Regardless, the frame 236 includes a pair of pinholes 242 in a transition or junction between the dilator tip 204 and the dilator body 202 but symmetrically distributed between sinistral and dextral sides of the dilator 200. A pin of a pair of pins 244 is disposed in each pinhole of the pinholes 242, and each blade of the blades 238 is rotatably mounted on one of the foregoing pins 244.

Notwithstanding the pins 244 upon which the blades 238 are rotatably mounted, the frame 236 includes a pair of blade-lock pins 246 proximal of the pinholes 242 in the transition or junction between the dilator tip 204 and the dilator body 202. The blade-lock pins 246 are configured to insert into the blade-lock holes 260 of the blades 238 when the blades 238 rotate their respective blade-lock holes 260 over the blade-lock pins 246 in the relatively late-dilating state of the dilator 200. Advantageously, both the blade-lock pins 246 and the blade-lock holes 260 function in concert to lock the blades 238 in the dilator body 202 in the relatively late-dilating state of the dilator 200, thereby ceasing to cut tissue around an insertion site even if continuing to insert the dilator 200 into the insertion site. In this way, the foregoing features provide an integrated single-use enforcement mechanism enforcing a single use of each dilator like the dilator 200.

Each blade of the blades 238 is disposed in an opposite side (e.g., the sinistral or dextral side) of the dilator 200 such that the blades 238 cut tissue on opposite sides of an insertion site upon insertion of the dilator 200 into the insertion site. However, the blades 238 are short of a distal end of the dilator 200 or the dilator tip 204 thereof. Having the blades 238 short of the distal end of the dilator 200 or the dilator tip 204 thereof allows at least the distal end of the dilator tip 204 to engage the insertion site before cutting the tissue around the insertion site.

Each blade of the blades 238 has an approximate shape of a geometric disk sector ◇ with a radius such as a leading radius of a leading edge 248 or a trailing radius of a trailing edge 250 as well as a blade edge 252 along an arc between the foregoing radii or edges 248 and 250. Each blade of the blades 238 includes a primary tissue catch 254 (e.g., a hook) extending from a leading corner of the blade where the leading edge 248 meets the blade edge 252. The primary tissue catch 254 is configured to catch the tissue around the insertion site, rotate its corresponding blade out from the dilator body 202, and cut the tissue around the insertion site as the dilator 200 is inserted into the insertion site. Notably, just the primary tissue catch 254 extends from its respective side of the dilator 200 in a ready-to-dilate state of the dilator 200. Each blade of the blades 238 also includes a secondary tissue catch 256 (e.g., a hook, but less pronounced than that of the primary tissue catch 254) in a midsection of the blade edge 252. The secondary tissue catch 256 is configured to further catch the tissue around the insertion site, further rotate its corresponding blade out from the dilator body 202, and further cut the tissue around the insertion site as the dilator 200 is further inserted into the insertion site. Each blade of the blades 238 also includes a tertiary tissue catch 258 including a trailing corner of the blade where the trailing edge 250 meets the blade edge 252. The tertiary tissue catch 258 is configured to catch the tissue around the insertion site and rotate its corresponding blade into the dilator body 202 without further cutting the tissue around the insertion site as the dilator 200 is inserted into the insertion site.

The blades 238 also have blade-lock holes 260, wherein each blade of the blades 238 has a blade-lock hole along the trailing edge 250 thereof. Such a blade-lock hole is configured to accept insertion of a blade-lock pin of the blade-lock pins 246 therein when its corresponding blade is rotated over the blade-lock pin in the relatively late-dilating state of the dilator 200. Advantageously, both the blade-lock holes 260 and the blade-lock pins 246 function in concert to lock their corresponding blades 238 in the dilator body 202 in the relatively late-dilating state of the dilator 200, thereby ceasing to cut tissue around an insertion site even if continuing to insert the dilator 200 into the insertion site. In this way, the foregoing features provide an integrated single-use enforcement mechanism enforcing a single use of each dilator like the dilator 100.

Figures 17, 18:
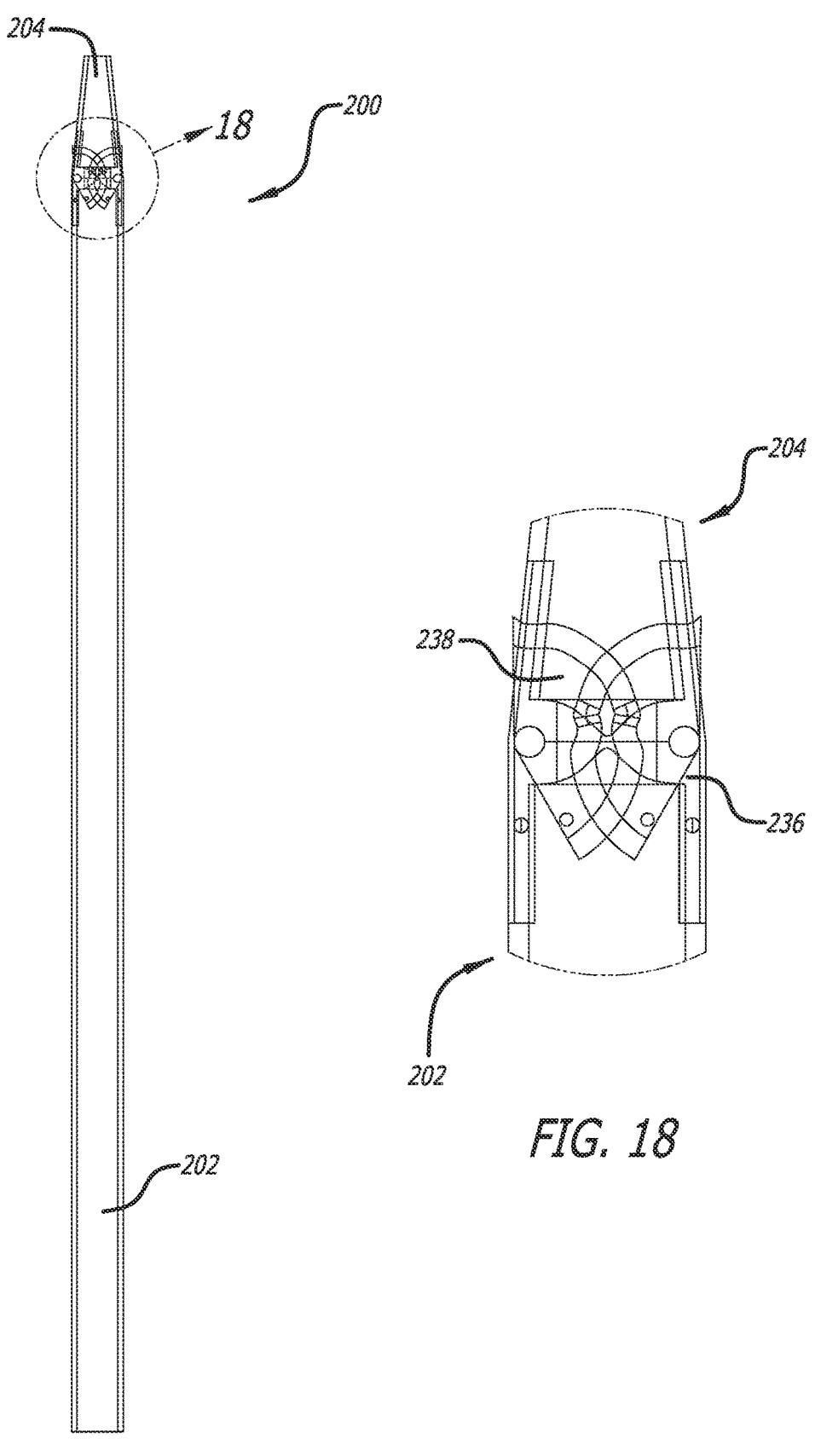
FIG. 17 illustrates a second tissue-cutting dilator in a ready-to-dilate state with proximally facing primary tissue catches of a pair of rotatable blades extending from sides of the dilator in accordance with some embodiments.
FIG. 18 illustrates a detailed view of a distal portion of the second tissue-cutting dilator in the ready-to-dilate state with the proximally facing primary tissue catches of the blades extending from the sides of the dilator in accordance with some embodiments.

FIGS. 17-26 illustrate the dilator 200 in various states thereof from the ready-to-dilate state of the dilator 200 through the relatively late-dilating state of the dilator 200, which, in turn, illustrates how features of the blades 238 including the various tissue catches (i.e., the primary tissue catch 254, the secondary tissue catch 256, and the tertiary tissue catch 258) thereof function when dilating a needle tract of an insertion site with the dilator 200. Indeed, FIGS. 17 and 18 illustrate the dilator 200 in the ready-to-dilate state of the dilator 200 with the primary tissue catch 254 of each blade of the blades 238 proximally facing and extending from the sides (e.g., the sinistral and dextral sides) of the dilator 200. Again, the primary tissue catch 254 are configured to catch the tissue around the insertion site, rotate the blades 238 out from the dilator body 202, and cut the tissue around the insertion site as the dilator 200 is inserted into the insertion site.

Figures 19, 20:
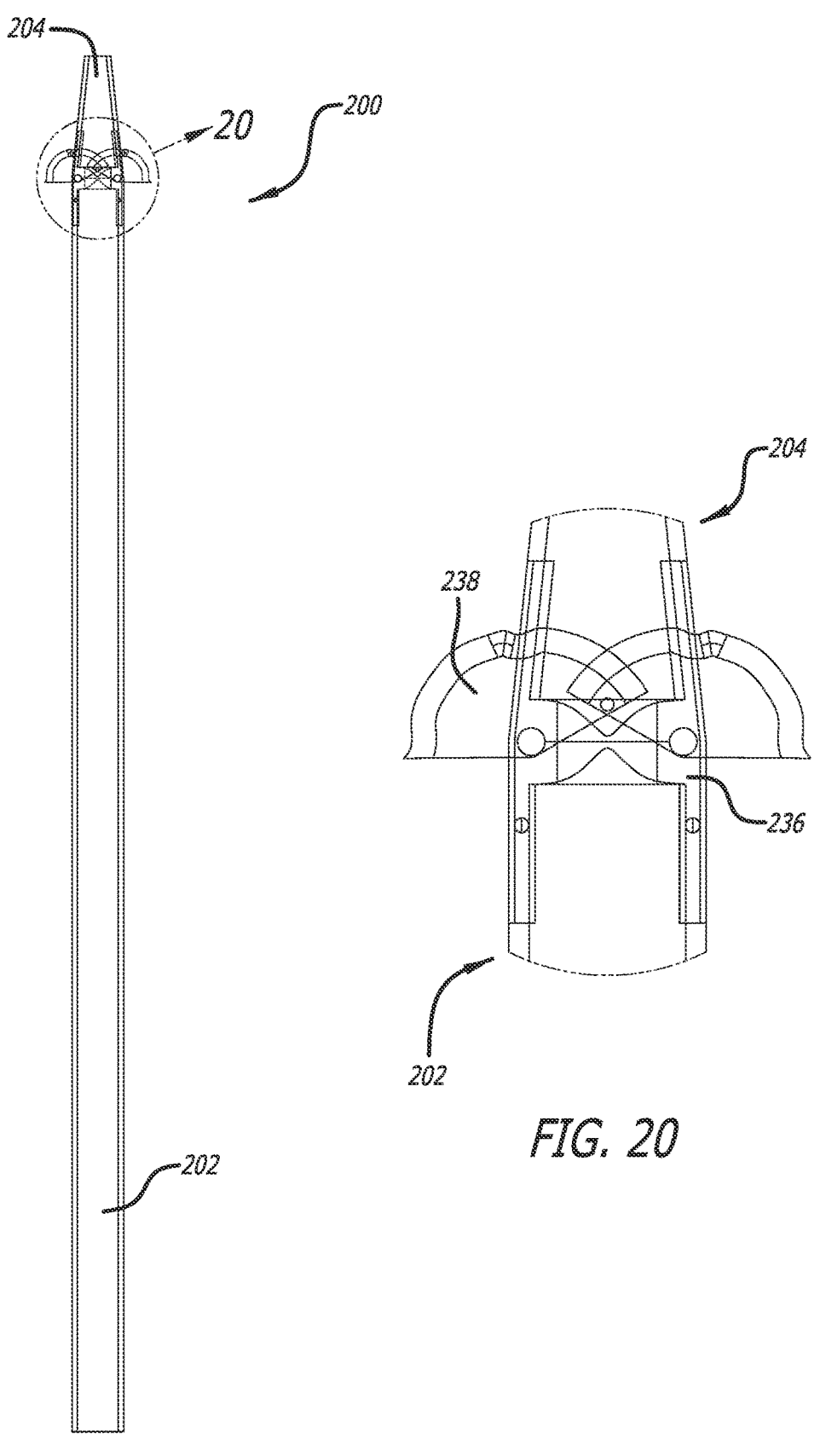
FIG. 19 illustrates the second tissue-cutting dilator in a relatively early-to-mid dilating state with proximally facing secondary tissue catches of the blades extending from the sides of the dilator in accordance with some embodiments.
FIG. 20 illustrates a detailed view of the distal portion of the second tissue-cutting dilator in the relatively early-to-mid dilating state with the proximally facing secondary tissue catches of the blades extending from the sides of the dilator in accordance with some embodiments.
Figures 21, 22:
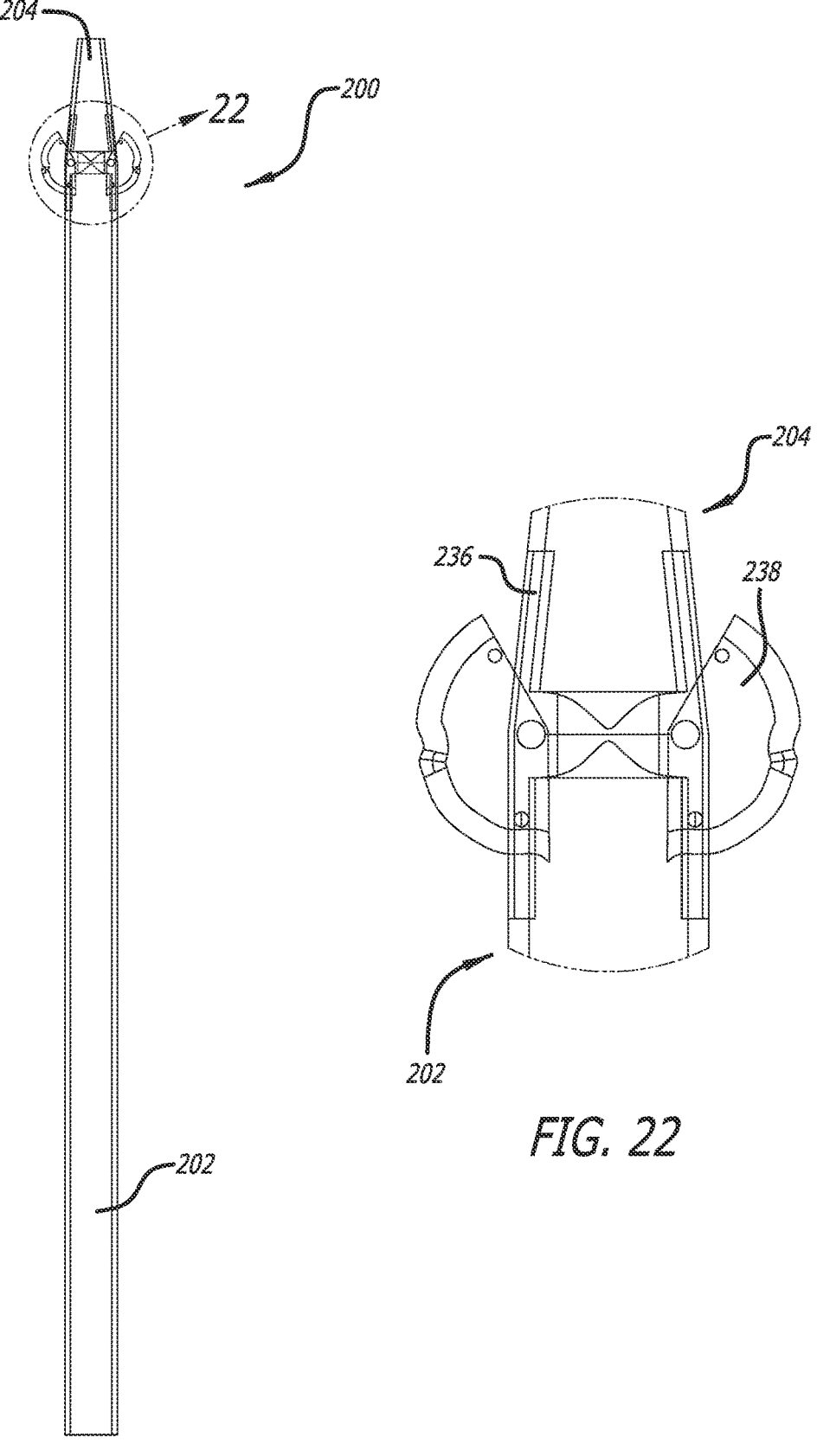
FIG. 21 illustrates the second tissue-cutting dilator in a mid-dilating state with proximally facing tertiary tissue catches of the blades extending from the sides of the dilator in accordance with some embodiments.
FIG. 22 illustrates a detailed view of the distal portion of the second tissue-cutting dilator in the mid-dilating state with the proximally facing tertiary tissue catches of the blades extending from the sides of the dilator in accordance with some embodiments.

FIGS. 19 and 20 illustrate the dilator 200 in a relatively early-to-mid dilating state of the dilator 200 with the secondary tissue catch 256 of each blade of the blades 238 proximally facing and extending from the sides of the dilator 200 in accordance with some embodiments. Again, the secondary tissue catch 256 is configured to further catch the tissue around the insertion site, further rotate the blades 238 out from the dilator body 202, and further cut the tissue around the insertion site as the dilator 200 is further inserted into the insertion site. FIGS. 21 and 22 illustrate the dilator 200 in the mid-dilating state of the dilator 200 with the tertiary tissue catch 258 of each blade of the blades 238 proximally facing extending from the sides of the dilator 200 in accordance with some embodiments. Again, the tertiary tissue catch 258 is configured to catch the tissue around the insertion site and rotate the blades 238 into the dilator body 202 without further cutting the tissue around the insertion site as the dilator 200 is inserted into the insertion site.

Figures 23, 24:
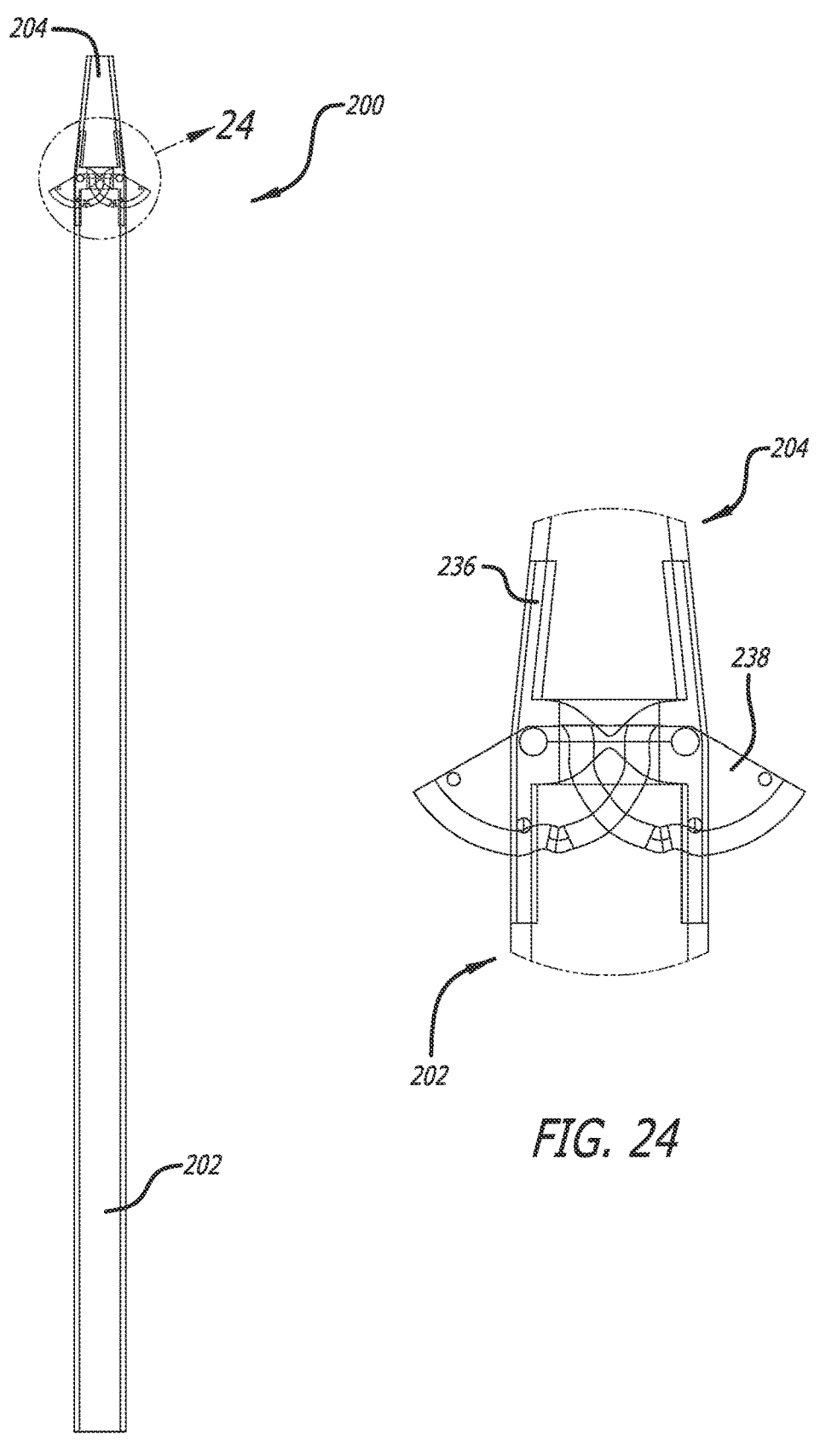
FIG. 23 illustrates the second tissue-cutting dilator in a relatively mid-to-late dilating state with tertiary tissue catches of the blades rotating back into the sides of the dilator in accordance with some embodiments.
FIG. 24 illustrates a detailed view of the distal portion of the second tissue-cutting dilator in the relatively mid-to-late dilating state with the tertiary tissue catches of the blades rotating back into the sides of the dilator in accordance with some embodiments.
Figures 25, 26:
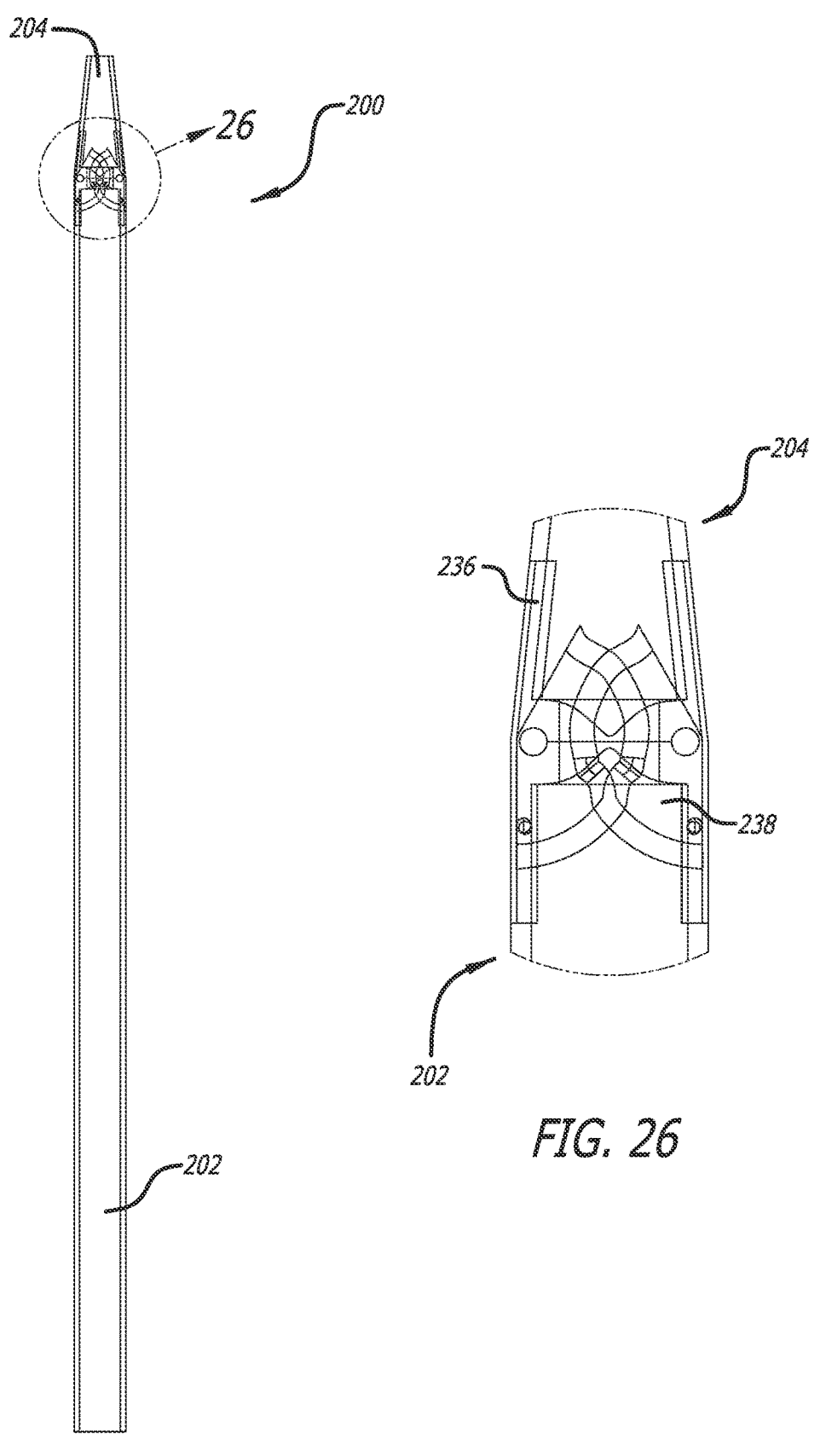
FIG. 25 illustrates the second tissue-cutting dilator in a relatively late-dilating state with the blades rotated back into the sides of the dilator in accordance with some embodiments.
FIG. 26 illustrates a detailed view of the distal portion of the second tissue-cutting dilator in the relatively late-dilating state with the blades rotated back into the sides of the dilator in accordance with some embodiments.
Figures 27, 28:
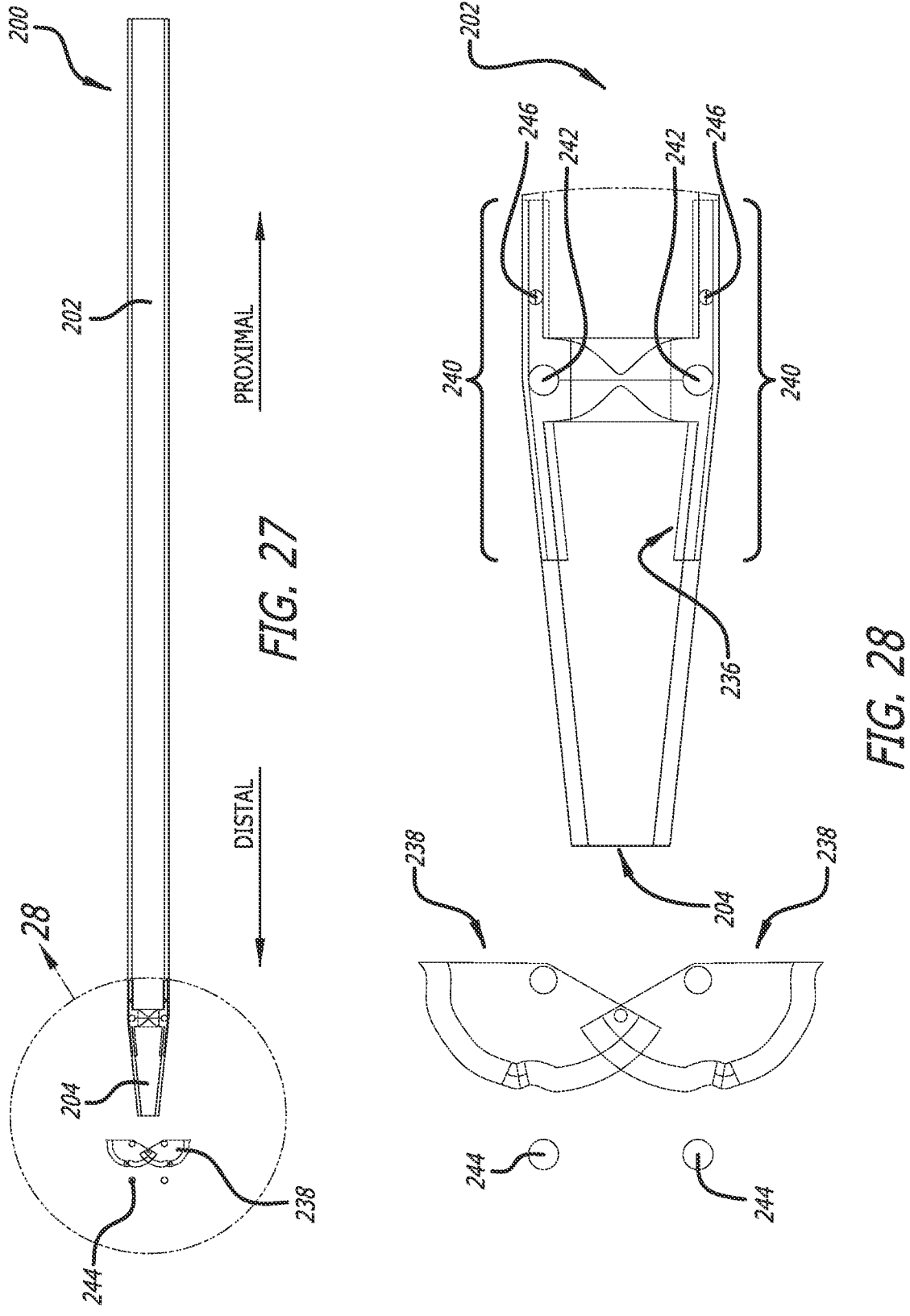
FIG. 27 illustrates an exploded view of the second tissue-cutting dilator in accordance with some embodiments.
FIG. 28 illustrates a detailed, exploded view of the distal portion of the second tissue-cutting dilator in accordance with some embodiments.
Figure 29:
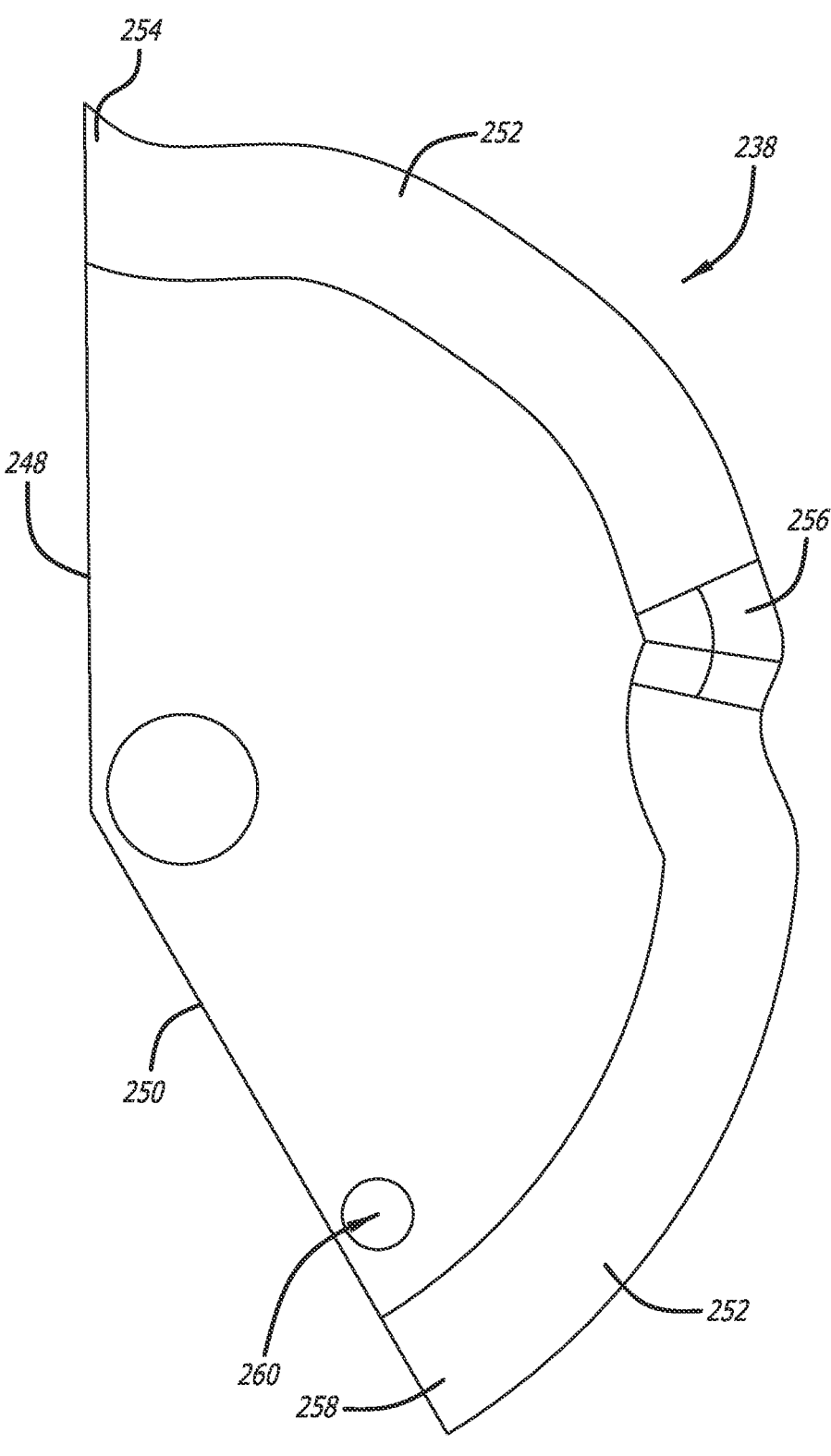
FIG. 29 illustrates a detailed view of a blade of the pair of blades in accordance with some embodiments.

FIGS. 23 and 24 illustrate the dilator 200 in a relatively mid-to-late dilating state of the dilator 200 with the tertiary tissue catch 258 of each blade of the blades 238 rotating back into the sides of the dilator 200 in accordance with some embodiments. Lastly, FIGS. 25 and 26 illustrate the dilator 200 in the relatively late-dilating state of the dilator 200 with the blades 238 rotated back into the sides of the dilator 200 in accordance with some embodiments. Notably, each blade of the blades 238 rotates about 330° from the ready-to-dilate state of the dilator 200 through the relatively late-dilating state of the dilator 200.

Methods

Methods include methods of using the dilator 100 or 200. For example, a method of using the dilator 100 or 200 includes one or more steps selected from a dilator-inserting step, a tissue-cutting step, and a ceasing step.

The dilator-inserting step includes inserting at least the distal end of the dilator tip 104 or 204 into a needle tract (e.g., a needle tract from an area of skin to a blood-vessel lumen) of an insertion site after the needle tract is established with an introducer needle. The dilator-inserting step commences dilation of tissue around the insertion site.

The tissue-cutting step includes cutting the tissue around the insertion site with the blades 122 or 238 while further inserting the dilator tip 104 or 204 into the insertion site. As set forth above, the blades 122 or 238 are disposed in the dilator 100 or 200 short of the distal end of the dilator tip 104 or 204 such that at least the distal end of the dilator tip 104 or 204 can engage the insertion site in the dilator-inserting step before cutting the tissue around the insertion site with the blades 122 or 238 in the tissue-cutting step.

The ceasing step includes ceasing to cut the tissue around the insertion site with the blades 122 or 238 while even further inserting the dilator tip 104 or 204 into the insertion site. When the dilator 100 is used, the blades 122 retract into the dilator 100 while even further inserting the dilator tip 104 into the insertion site. But when the dilator 200 is used, the blades 238 rotate into the dilator 200 while even further inserting the dilator tip 204 into the insertion site.

Adverting to the dilator 100 for description thereof in the foregoing steps, the cap 108 of the dilator 100 is made to proximally slide over the dilator 100 by interaction with skin around the insertion site while inserting the dilator tip 104 into the insertion site during the dilator-inserting step. Proximally sliding the cap 108 over the dilator 100 exposes the blades 122 for the cutting of the tissue around the insertion site. The cap 108 is further made to proximally slide over the dilator 100 by the interaction with the skin around the insertion site while further inserting the dilator tip 104 into the insertion site during the tissue-cutting step. Proximally sliding the cap 108 further over the dilator 100 keeps the blades 122 exposed for the cutting of the tissue around the insertion site. The cap 108 is even further made to proximally slide over the dilator 100 by the interaction of the skin around the insertion site while even further inserting the dilator tip 104 into the insertion site during the ceasing step. Proximally sliding the cap 108 even further over the dilator 100 makes the cap protrusions 134 extending through the guide slots 110 of the dilator 100 to engage the catch plate 120 and retract the blades 122 into the dilator 100 for the ceasing to cut the tissue around the insertion site with the blades 122.

Adverting to the dilator 200 for description thereof in the foregoing steps, the primary tissue catch 254 of each blade of the blades 238 in the corresponding leading corners of the blades 238 extend from the sides of the dilator 200 and catch skin around the insertion site while inserting the dilator tip 204 into the insertion site during the dilator-inserting step. Catching the skin around the insertion site while inserting the dilator tip 204 into the insertion site rotates the blades 238 out of the dilator 200 for the cutting of the tissue around the insertion site. The secondary tissue catch 256 of each blade of the blades 238 in the midsections of the blades 238 catch the tissue around the insertion site while further inserting the dilator tip 204 into the insertion site during the tissue-cutting step. Catching the skin around the insertion site while further inserting the dilator tip 204 into the insertion site continues to rotate the blades 238 out of the dilator 200 for the cutting of the tissue around the insertion site. The tertiary tissue catch 258 of each blade of the blades 238 in the corresponding trailing corners of the blades 238 catch the tissue around the insertion site while even further inserting the dilator tip 204 into the insertion site during the ceasing step. Catching the skin around the insertion site while even further inserting the dilator tip 204 into the insertion site rotates the blades 238 into the dilator 200 for the ceasing to cut the tissue around the insertion site with the blades 238.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. A tissue-cutting dilator, comprising:

an elongate dilator body including a plurality of longitudinal guide slots along a distal portion of the dilator body;

a dilator tip formed in the distal portion of the dilator body or coupled to a distal end of the dilator body, the dilator tip including a plurality of blade slots;

a plurality of retractable blades disposed in the dilator body, the plurality of retractable blades configured to extend through the plurlaity of blade slots in at least a ready-to-dilate state of the tissue-cutting dilator to cut tissue around an insertion site upon insertion into the insertion site; and a cap slidably disposed over the dilator body, the cap covering the dilator tip in at least the ready-to-dilate state of the tissue-cutting dilator, the cap comprising a plurality of cap protrusions, wherein the plurality of longitudinal guide slots are configured to accept the plurality of cap protrusions when proximally sliding the cap over the dilator body.

2. The dilator of claim 1, wherein the plurality of longitudinal guide slots terminate as grooves in the dilator tip, the grooves providing reinforcing structure to the dilator tip over that provided by the plurality of longitudinal guide slots for tissue dilation with the dilator tip.

3. The dilator of claim 1, wherein distal ends of the plurality of retractable blades are short of a distal end of the tissue-cutting dilator or the dilator tip thereof, thereby allowing at least the distal end of the dilator tip to engage the insertion site before cutting the tissue around the insertion site.

4. The dilator of claim 1, wherein the plurality of retractable blades include two intersecting blades coupled to a catch plate slidably disposed in the dilator body proximal of the dilator tip.

5. The dilator of claim 4, wherein the two intersecting blades provide four orthogonal blade edges, each blade edge of the four orthogonal blade edges orthogonal to its immediately adjacent blade edges.

6. The dilator of claim 4, wherein the catch plate is proximal of the dilator tip in the ready-to-dilate state of the tissue-cutting dilator.

7. The dilator of claim 4, wherein the plurality of cap protrusions are protruding toward a central axis of the tissue-cutting dilator, the plurality of cap protrusions disposed in at least a distal portion of the cap such that the plurality of cap protrusions can engage the catch plate when proximally sliding the cap over the dilator body past the dilator tip, thereby retracting the plurality of retractable blades into the dilator body for dilation with the tissue-cutting dilator without further cutting the tissue around the insertion site.

8. The dilator of claim 7, wherein the cap is configured to proximally slide over the dilator body by interaction with skin around the insertion site as the dilator tip is inserted into the insertion site.

9. The dilator of claim 7, wherein the catch plate includes a plurality of notches configured to engage the plurality of cap protrusions in the distal portion of the cap, the plurality of notches in the catch plate orthogonal to the plurality of retractable blades.

10. The dilator of claim 7, wherein the plurality of cap protrusions are further disposed in a proximal portion of the cap, the plurality of cap protrusions in the proximal portion of the cap configured to slide in the plurality of longitudinal guide slots and obviate any play between the proximal portion of the cap and the dilator body thereunder.

11. The dilator of claim 4, wherein the catch plate includes a stabilizer integral with the catch plate or coupled to a proximal end of the catch plate, the stabilizer including split legs configured to slidably engage an inner wall of the dilator body and mitigate tilting of the catch plate within the dilator body, thereby keeping the plurality of retractable blades properly aligned in the dilator body and avoiding blade jams.

12. The dilator of claim 4, further comprising a compression spring between a proximal end of the catch plate and a seat therefor in the dilator body, the compression spring is configured to mitigate tilting of the catch plate within the dilator body, thereby keeping the plurality of retractable blades properly aligned in the dilator body and avoiding blade jams.

13. The dilator of claim 12, wherein the compression spring is further configured to keep the plurality of retractable blades extending through the plurality of blade slots in the ready-to-dilate state of the tissue-cutting dilator whether or not the tissue-cutting dilator is pointed, in part, along a gravitational vector.

14. A tissue-cutting dilator, comprising:

an elongate dilator body including a plurality of longitudinal guide slots along a distal portion of the dilator body;

a dilator tip formed in the distal portion of the dilator body or coupled to a distal end of the dilator body, the dilator tip including a plurality of blade slots;

two intersecting retractable blades coupled to a catch plate slidably disposed in the dilator body, the two intersecting retractable blades configured to extend through the plurality of blade slots in at least a ready-to-dilate state of the tissue-cutting dilator to cut tissue around an insertion site upon insertion into the insertion site;

a cap slidably disposed over the dilator body, the cap covering the dilator tip in at least the ready-to-dilate state of the tissue-cutting dilator; and a compression spring between a proximal end of the catch plate and a seat therefor in the dilator body.

15. The dilator of claim 14, wherein the compression spring is configured to mitigate tilting of the catch plate within the dilator body, thereby keeping the two intersecting retractable blades properly aligned in the dilator body and avoiding blade jams.

16. The dilator of claim 15, wherein the compression spring is further configured to mitigate tilting of the catch plate within the dilator body, thereby keeping the two intersecting retractable blades properly aligned in the dilator body and avoiding blade jams.

17. The dilator of claim 14, wherein the catch plate is proximal of the dilator tip in the ready-to-dilate state of the tissue-cutting dilator.

18. The dilator of claim 14, wherein the two intersecting retractable blades provide four orthogonal blade edges, each blade edge of the four orthogonal blade edges orthogonal to its immediately adjacent blade edges.

19. The dilator of claim 14, wherein the catch plate includes a stabilizer integral with the catch plate or coupled to a proximal end of the catch plate, the stabilizer including split legs configured to slidably engage an inner wall of the dilator body and mitigate tilting of the catch plate within the dilator body, thereby keeping the two intersecting retractable blades properly aligned in the dilator body and avoiding blade jams.

20. The dilator of claim 14, wherein the cap includes a plurality of cap protrusions protruding toward a central axis of the tissue-cutting dilator, the plurality of cap protrusions disposed in at least a distal portion of the cap such that the plurality of cap protrusions engage the catch plate when proximally sliding the cap over the dilator body past the dilator tip, thereby retracting the two intersecting blades into the dilator body for dilation with the tissue-cutting dilator without further cutting the tissue around the insertion site.

* * * * *